(12) United States Patent
Cerepak et al.

(10) Patent No.: US 12,245,785 B2
(45) Date of Patent: Mar. 11, 2025

(54) BALLOON DILATION CATHETER FOR USE IN SINUS DRAINAGE PATHWAYS

(71) Applicant: Entellus Medical, Inc., Maple Grove, MN (US)

(72) Inventors: Ryan Cerepak, Champlin, MN (US); Tony Hanson, Plymouth, MN (US); Alexander Houck, Hopkins, MN (US); John Drontle, Buffalo, MN (US)

(73) Assignee: Stryker Corporation, Portage, MI (US)

( * ) Notice: Subject to any disclaimer, the term of this patent is extended or adjusted under 35 U.S.C. 154(b) by 417 days.

(21) Appl. No.: 17/772,462

(22) PCT Filed: Oct. 29, 2020

(86) PCT No.: PCT/US2020/057931
§ 371 (c)(1),
(2) Date: Apr. 27, 2022

(87) PCT Pub. No.: WO2021/087094
PCT Pub. Date: May 6, 2021

(65) Prior Publication Data
US 2022/0378454 A1    Dec. 1, 2022

Related U.S. Application Data

(60) Provisional application No. 62/928,324, filed on Oct. 30, 2019.

(51) Int. Cl.
*A61B 17/24* (2006.01)
*A61B 17/00* (2006.01)
(Continued)

(52) U.S. Cl.
CPC .............. *A61B 17/24* (2013.01); *A61B 90/30* (2016.02); *A61M 29/02* (2013.01); *B29C 65/04* (2013.01);
(Continued)

(58) Field of Classification Search
CPC ................... A61B 17/24; A61B 90/30; A61B 2017/00526; A61B 2017/00557;
(Continued)

(56) References Cited

U.S. PATENT DOCUMENTS

2010/0312101 A1*  12/2010  Drontle ................. A61B 17/24
                                                        606/196
2011/0172520 A1    7/2011  Lentz
(Continued)

FOREIGN PATENT DOCUMENTS

CN     209 301 948 U    8/2019
EP       1 683 540 A1   7/2006
(Continued)

OTHER PUBLICATIONS

International Search Report mailed on Mar. 2, 2021, issued in connection with International Application No. PCT/US2020/057931, filed on Oct. 29, 2020, 8 pages.
(Continued)

*Primary Examiner* — Jocelin C Tanner
(74) *Attorney, Agent, or Firm* — McDonnell Boehnen Hulbert & Berghoff LLP

(57) ABSTRACT

The present disclosure provides a balloon dilation catheter that includes a handle (102), a substantially rigid inner guide member (108) coupled to the handle, a shaft (118) arranged over the inner guide member, a balloon (120) coupled to the inner guide member, and a polymer ball tip (122) positioned at a distal end of the balloon. To treat a sinus drainage pathway of a subject using the balloon dilation catheter, the substantially rigid inner guide member is positioned into the drainage pathway of the sinus of the subject via a nasal passageway. The balloon is then inflated to expand or otherwise remodel the drainage pathway.

11 Claims, 7 Drawing Sheets

(51) Int. Cl.
*A61B 90/30* (2016.01)
*A61M 29/02* (2006.01)
*B29C 65/04* (2006.01)
*B29K 705/12* (2006.01)
*B29L 31/00* (2006.01)

(52) U.S. Cl.
CPC ............... *A61B 2017/00526* (2013.01); *A61B 2017/00557* (2013.01); *A61B 2017/246* (2013.01); *A61B 2090/306* (2016.02); *A61M 2210/0618* (2013.01); *A61M 2210/0681* (2013.01); *B29K 2705/12* (2013.01); *B29L 2031/7543* (2013.01)

(58) Field of Classification Search
CPC ....... A61B 2017/246; A61B 2090/306; A61M 25/0041; A61M 25/0068; A61M 25/10; A61M 25/0067; A61M 29/02; A61M 2025/0166; A61M 2025/0081; A61M 2210/0681; B29C 65/04; B29K 2705/12; B29K 2031/7543
USPC ......................................................... 606/196
See application file for complete search history.

(56) References Cited

U.S. PATENT DOCUMENTS

| | | |
|---|---|---|
| 2012/0071727 A1 | 3/2012 | Hanson et al. |
| 2013/0030458 A1 | 1/2013 | Drontle et al. |
| 2014/0276328 A1 | 9/2014 | Kesten et al. |
| 2015/0073467 A1 | 3/2015 | Eaton |

FOREIGN PATENT DOCUMENTS

| | | | |
|---|---|---|---|
| EP | 3 476 271 A2 | 5/2019 | |
| WO | 2008/088662 A2 | 7/2008 | |
| WO | WO-2010014799 A1 * | 2/2010 | ............. A61B 1/233 |

OTHER PUBLICATIONS

Written Opinion mailed on Mar. 2, 2021, issued in connection with International Application No. PCT/US2020/057931, filed on Oct. 29, 2020, 8 pages.

* cited by examiner

BALLOON DILATION CATHETER FOR USE IN SINUS DRAINAGE PATHWAYS

RELATED APPLICATIONS

This application is the US national phase under 35 U.S.C. § 371 of International Application No. PCT/US2020/057931, filed on Oct. 29, 2020, which claims priority to U.S. Provisional Application No. 62/928,324 entitled "Balloon Dilation Catheter for Use in Sinus Drainage Pathways," filed on Oct. 30, 2019, the contents of which are hereby incorporated by reference in their entirety.

FIELD

The field of the invention generally relates to balloon inflation devices and methods. More particularly, the field of the invention relates to balloon dilation devices and methods for the treatment of sinusitis.

BACKGROUND

Unless otherwise indicated herein, the materials described in this section are not prior art to the claims in this application and are not admitted to be prior art by inclusion in this section.

Sinusitis is a condition affecting over 35 million Americans, and similarly large populations in the rest of the developed world. Sinusitis occurs when one or more of the four paired sinus cavities (i.e., maxillary, ethmoid, frontal, sphenoid) becomes obstructed, or otherwise has compromised drainage. Normally the sinus cavities, each of which are lined by mucosa, produce mucous which is then moved by beating cilia from the sinus cavity out to the nasal cavity and down the throat. The combined sinuses produce approximately one liter of mucous daily, so the effective transport of this mucous is important to sinus health.

Each sinus cavity has a drainage pathway or outflow tract opening into the nasal passage. This drainage passageway can include an ostium, as well as a "transition space" in the region of the ostia, such as the "frontal recess," in the case of the frontal sinus, or an "ethmoidal infundibulum," in the case of the maxillary sinus. When the mucosa of one or more of the ostia or regions near the ostia become inflamed, the egress of mucous is interrupted, setting the stage for an infection and/or inflammation of the sinus cavity, i.e., sinusitis. Though many instances of sinusitis may be treatable with appropriate medicates, in some cases sinusitis persists for months or more, a condition called chronic sinusitis, and may not respond to medical therapy. Some patients are also prone to multiple episodes of sinusitis in a given period of time, a condition called recurrent sinusitis.

Balloon dilation has been applied to treat constricted sinus passageways for the treatment of sinusitis. These balloon dilation devices typically involve the use of an inflatable balloon located at the distal end of a catheter such as a balloon catheter. Generally, the inflatable balloon is inserted into the constricted sinus passageway in a deflated state. The balloon is then expanded to open or reduce the degree of constriction in the sinus passageway being treated to facilitate better sinus drainage and ventilation. At the same time most, if not all, of the functional mucosal tissue lining of the sinuses and their drainage passageways are preserved.

While balloon dilation catheter systems exist for use in dilating sinus drainage pathways, improved balloon dilation catheter systems, methods of manufacture, and methods of use may be desirable.

SUMMARY

The present disclosure is related to balloon dilation catheter, methods of manufacture, and methods of use. More specifically, the present disclosure relates to balloon dilation catheter systems for treating nasal afflictions such as sinusitis.

In one aspect, the present disclosure provides a balloon dilation catheter for dilating sinus drainage pathways. The balloon dilation catheter includes a handle having a proximal end and a distal end, the handle configured to be gripped by an operator. The balloon dilation catheter also includes a substantially rigid inner guide member having a distal end and a proximal end. The substantially rigid inner guide member includes a lumen extending between the distal end and the proximal end of the substantially rigid inner guide member. The substantially rigid inner guide member extends longitudinally from the distal end of the handle. The distal end of the substantially rigid inner guide member includes a curved portion with a radius of curvature greater than zero. The balloon dilation catheter also includes a shaft arranged over the substantially rigid inner guide member. The shaft is fixed relative to the substantially rigid inner guide member. The balloon dilation catheter also includes a balloon coupled to the distal end of the substantially rigid inner guide member. The balloon is positioned over the curved portion of the substantially rigid inner guide member. The balloon dilation catheter also includes a polymer ball tip positioned at a distal end of the balloon. The polymer ball tip is formed from excess balloon material such that the polymer ball tip is directly coupled to the distal end of the balloon. The polymer ball tip is further coupled to the distal end of the substantially rigid inner guide member.

In another aspect, the present disclosure provides a method of treating a sinus drainage pathway of a patient. The method includes (a) providing the balloon dilation catheter of the first aspect, (b) directing the distal end of the substantially rigid inner guide member into a head of a patient through a nostril, (c) directing the distal end of the substantially rigid inner guide member to a desired position within the sinus drainage pathway, and (d) inflating the balloon to dilate tissue defining the desired position of the sinus drainage pathway.

In yet another aspect, the present disclosure provides a method manufacturing a balloon dilation catheter. The method includes (a) forming a handle having a proximal end and a distal end, (b) coupling a proximal end of a substantially rigid inner guide member to an interior of the handle, wherein the substantially rigid inner guide member includes a lumen extending between a distal end and the proximal end of the substantially rigid inner guide member, wherein the substantially rigid inner guide member extends longitudinally from the distal end of the handle, and wherein the distal end of the substantially rigid inner guide member includes a curved portion with a radius of curvature greater than zero, (c) positioning a shaft over the substantially rigid inner guide member and coupling the shaft to the interior of the handle, wherein the shaft is fixed relative to the substantially rigid inner guide member, (d) coupling a balloon to the distal end of the substantially rigid inner guide member, wherein the balloon is positioned over the curved portion of the substantially rigid inner guide member, and (e) forming a polymer ball tip at the distal end of the balloon from excess balloon material such that the polymer ball tip is directly coupled to the distal end of the balloon, wherein the polymer ball tip is further coupled to the distal end of the substantially rigid inner guide member.

These as well as other aspects, advantages, and alternatives, will become apparent to those of ordinary skill in the art by reading the following detailed description, with reference where appropriate to the accompanying drawings.

DETAILED DESCRIPTION

Figure 1:
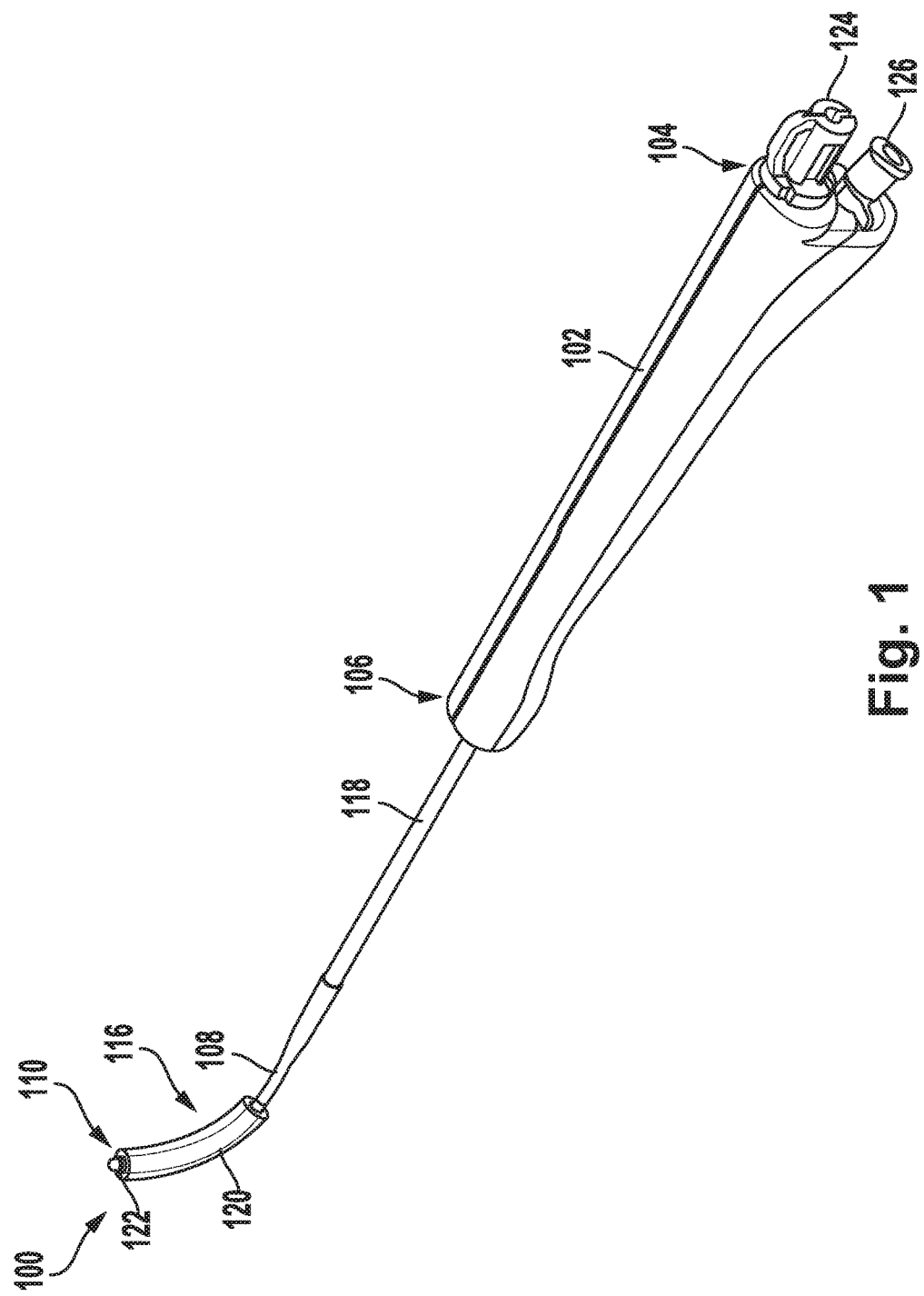
FIG. 1 is a perspective view of the balloon dilation catheter, according to an example.
Figure 2:
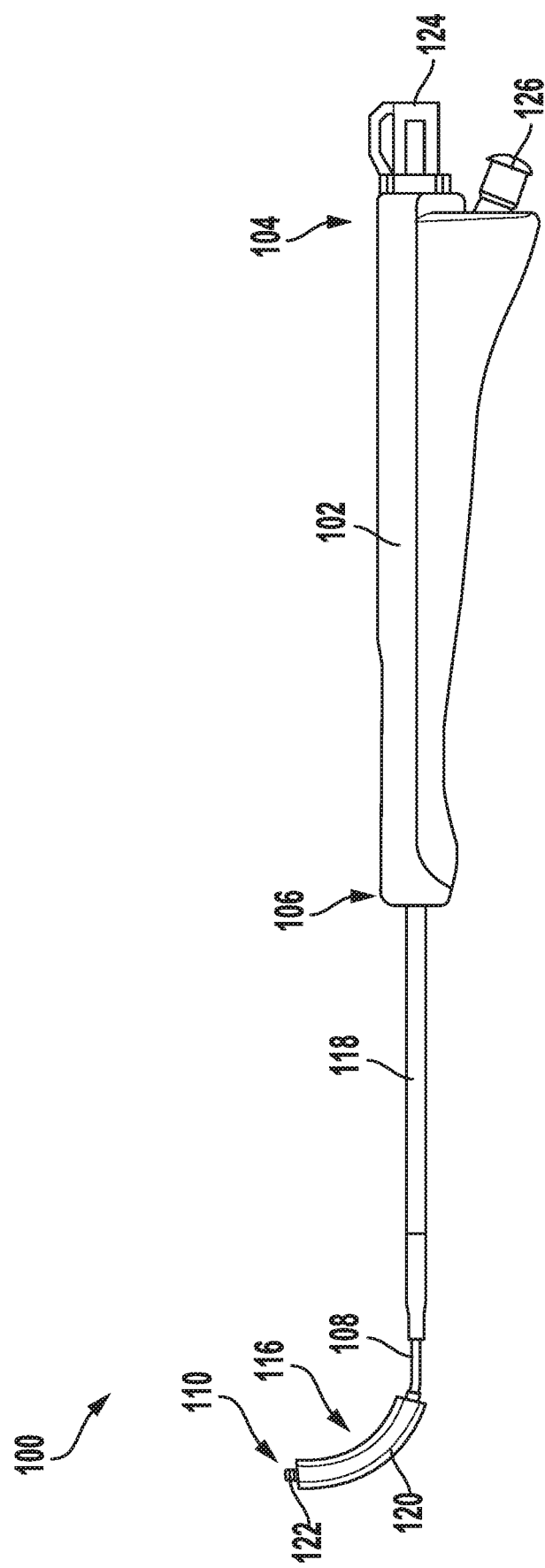
FIG. 2 is a side view of the balloon dilation catheter of FIG. 1, according to an example.

Example methods and systems are described herein. It should be understood that the words "example," "exemplary," and "illustrative" are used herein to mean "serving as an example, instance, or illustration." Any example or feature described herein as being an "example," being "exemplary," or being "illustrative" is not necessarily to be construed as preferred or advantageous over other examples or features. The examples described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other examples may include more or less of each element shown in a given Figure. Further, some of the illustrated elements may be combined or omitted. Yet further, an example may include elements that are not illustrated in the Figures.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The limitations of the following claims are not written in means-plus-function format and are not intended to be interpreted based on 35 U.S.C. § 112(f), unless and until such claim limitations expressly use the phrase "means for" followed by a statement of function void of further structure.

By the term "about," "approximately," or "substantially" with reference to amounts or measurement values described herein, it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Illustrative, non-exhaustive examples, which may or may not be claimed, of the subject matter according the present disclosure are provided below.

With reference to the Figures, FIG. 1 illustrates a perspective view of a balloon dilation catheter 100 for dilating sinus drainage pathways, according to an example. As shown in FIG. 1, the balloon dilation catheter 100 includes a handle 102 having a proximal end 104 and a distal end 106. The handle 102 is configured to be gripped by an operator when in use. The balloon dilation catheter 100 also includes a substantially rigid inner guide member 108 having a distal end 110 and a proximal end 112. The substantially rigid inner guide member 108 includes a lumen 114 extending between the distal end 110 and the proximal end 112 of the substantially rigid inner guide member 108. The substantially rigid inner guide member 108 extends longitudinally from the distal end 106 of the handle 102. The distal end 110 of the substantially rigid inner guide member 108 includes a curved portion 116 with a radius of curvature greater than zero. The nature and degree of the curved portion 116 may correspond to the desired treatment zone, as discussed in additional detail below.

The balloon dilation catheter 100 also includes a shaft 118 arranged over the substantially rigid inner guide member 108. The shaft 118 is fixed relative to the substantially rigid inner guide member 108. Further, the substantially rigid inner guide member 108 and the shaft 118 are both fixed relative to the handle 102. The balloon dilation catheter 100 also includes a balloon 120 coupled to the distal end 110 of the substantially rigid inner guide member 108. The balloon 120 is positioned over the curved portion 116 of the substantially rigid inner guide member 108. In one example, the balloon 120 is fixed relative to the shaft 118 and further fixed relative to the substantially rigid inner guide member 108. The balloon dilation catheter 100 also includes a polymer ball tip 122 positioned at a distal end of the balloon 120. The polymer ball tip 122 is formed from excess balloon material such that the polymer ball tip 122 is directly coupled to the distal end of the balloon 120, and the polymer ball tip 122 is further coupled to the distal end 110 of the substantially rigid inner guide member 108.

Figure 3:
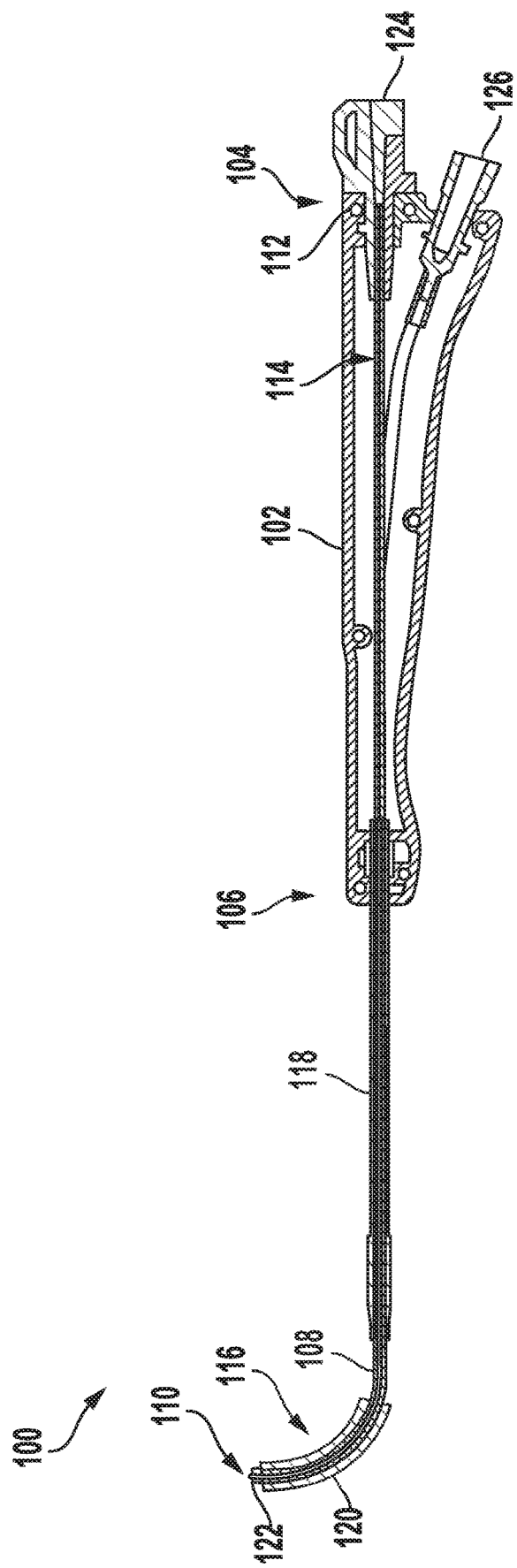
FIG. 3 is a cross-sectional view of the balloon dilation catheter of FIG. 1, according to an example.

The substantially rigid inner guide member 108 may have an inner diameter in a range of between about 0.508 mm and 1.27 mm, and preferably between about 0.9144 mm and 1.016 mm. In addition, the substantially rigid inner guide member 108 may have a wall thickness in a range of between about 0.127 mm and about 0.508 mm, and preferably between about 0.2032 mm and 0.3048 mm. In another example, the distal end 110 of the substantially rigid inner guide member 108 has a diameter of between about 1 and about 3 millimeters. The substantially rigid inner guide member 108 may have a length of about 177.8 mm to about 279.4 mm from the distal end 110 to the proximal end 112 when loaded into the handle 102, although other dimensions may be used. In one example, the proximal end 112 of the substantially rigid inner guide member 108 is secured within an interior of the handle 102, as shown in FIG. 3. Further, the substantially rigid inner guide member 108 may be sealed to the handle 102, for example in a press-fit type sealing arrangement. Other coupling mechanisms are possible as well.

In one example, the substantially rigid inner guide member 108 comprises a precipitation-hardened material, such as 17-7 precipitation-hardened stainless steel as a non-limiting example. As such, the distal end 110 of the substantially rigid inner guide member 108 may be intractable such that the radius of curvature of the curved portion 116 of the substantially rigid inner guide member 108 is constant and cannot be shaped by the operator. Such an arrangement ensures that the balloon dilation catheter 100 can only be used in the anatomy corresponding to the manufactured radius of curvature of the curved portion 116 of the substantially rigid inner guide member 108.

As discussed above, the balloon dilation catheter 100 also includes a polymer ball tip 122 positioned at the distal end of the balloon 120. The polymer ball tip 122 may be bulbous in shape in order to make the distal end of the substantially rigid inner guide member 108 more atraumatic. The outer diameter of the polymer ball tip 122 is preferably between about 1 mm and about 3 mm. As discussed above, the polymer ball tip 122 is formed from excess balloon material such that the polymer ball tip 122 is directly coupled to the distal end of the balloon 120, and the polymer ball tip 122 is further coupled to the distal end 110 of the substantially rigid inner guide member 108. Such an arrangement positions the balloon 120 right against the distal end 110 of the substantially rigid inner guide member 108, which enables the operator to reach the desired anatomy with less of the balloon dilation catheter 100 positioned in the sinus drainage pathway of the patient. As such, the balloon dilation catheter 100 may provide increased comfort to the patient while still providing access for treatment of the desired anatomy.

The balloon 120 is mounted on the substantially rigid inner guide member 108 so as to form a fluidic seal between the two components. The balloon 120 may be bonded to the substantially rigid inner guide member 108 using a weld, adhesive, or the like. Alternately, the balloon 120 may be secured to the substantially rigid inner guide member 108 using a mechanical connection. Generally, any technique known to those skilled in the art may be used to secure to the balloon 120 to the substantially rigid inner guide member 108. The balloon 120 generally takes on a cylindrical-shape when inflated. While not limited to specific dimensions, the inflated balloon 120 has a diameter within the range of about 3 mm to about 9 mm, and more preferably a diameter within the range of about 5 to about 7 mm when inflated. The length of the balloon 120 may generally fall within the range of about 10 mm to 25 mm although other lengths may be used. The balloon 120 is preferably formed of high strength but flexible polymeric materials such as polyamides (e.g., Nylon), PEBAX or the like. The balloon 120 may be "blow molded" to a relatively thin wall thickness, and capable of holding relatively high pressures from about 6 atmospheres to about 20 atmospheres of inflation pressure. The balloon 120 is inflated using a fluid which is typically a liquid such as water or saline.

As shown in the cross-sectional view of the balloon dilation catheter 100 in FIG. 3, the proximal end 104 of the handle 102 includes a first port 124 and a second port 126. The first port 124 may be configured with a connection interface such as a Luer connector or any other connector known to those skilled in the art. The first port 124 may be integrally formed with the handle 102 or, alternatively, the first port 124 may be a separate structure that is secured to the handle 102 during assembly. As seen in FIG. 3, the proximal end 112 of the substantially rigid inner guide member 108 forms a sealing arrangement with the first port 124. The substantially rigid inner guide member 108 optionally includes a lumen disposed therein that may be used to provide aspiration functionality via an aspiration device (not shown) coupled to first port 124. Aspiration functionality permits the removal of blood and other secretions. This makes it easier to visualize the placement of the balloon dilation catheter 100. The rigidity of the substantially rigid inner guide member 108 may enable the balloon dilation catheter 100 to be positioned without the need of a separate guiding catheter or guide wire.

In one example, the first port 124 comprises an adjustable connector configured to receive a guidewire. The adjustable connector enables the operator to adjust a position of a distal end of the guidewire in relation to the distal end of the substantially rigid inner guide member 108. In one example, the adjustable connector of the first port 124 comprises a threaded connection that enables the operator to adjust a position of a distal end of the guidewire in relation to the distal end of the substantially rigid inner guide member 108 by rotating the adjustable connector. In another example, the adjustable connector of the first port 124 comprises a rotatable connection including one or more tabs that are compressed as the operator rotates the adjustable connector. Other examples of adjustable connectors are possible as well.

As further illustrated in FIG. 3, the balloon dilation catheter 100 further includes a second port 126 which may be constructed in the same or similar manner as the first port 124, as described above. The second port 126 is in fluid communication with the balloon 120 via an inflation lumen. In this regard, inflation fluid from an inflation device (not shown) is able to pass through the second port 126 and into the inflation lumen. The second port 126 may be configured with a connection interface such as a Luer connector. The fluid then is able to travel along the length of the inflation lumen, where the fluid enters the interior of the balloon 120. The inflation fluid is thus able to inflate the balloon 120 upon actuation of the inflation device.

The balloon dilation catheter 100 may further include a guidewire is arranged within the lumen 114 of the substantially rigid inner guide member 108. In one example, the guidewire is a tracking element for use with an image guided surgery system. The tracking element may include an antenna, transmitter, optical reflectors, or the like that communicates a wireless signal that is then received and processed to determine the orientation and/or positioning of the balloon dilation catheter 100. In certain embodiments, more than one tracking element may be disposed on the balloon dilation catheter 100. Data regarding the orientation and/or positioning of the balloon dilation catheter 100 may then be processed and displayed on the display for viewing by the physician. For example, image guided surgery is becoming increasingly commonplace, permitting physicians to review real time actual or virtual images of a particular device within a subject during a surgical procedure. In examples, the tracking element permits accurate tracking of the distal end of the balloon dilation catheter 100 such that an image of distal portion of the balloon dilation catheter 100 may be superimposed on a patient's anatomical imagery. For example, a previously conducted computed tomography (CT) scan of the patient may be used to generate a visual image of the patient's anatomical regions of interest. Based on the location of the tracking element, an image guided surgery (IGS) system can then superimpose an image of the balloon dilation catheter 100 onto the image to better enable the physician to manipulate and orient the balloon dilation catheter 100. The use of CT guidance to position the balloon dilation catheter 100 may be preferred because the device may be positioned by the operator with just a single hand, while viewing the CT image interface (e.g., display) at the same time the handle 102 is manipulated. Optionally, the balloon dilation catheter 100 may be initially positioned using and endoscope or other visualization tool. For instance, a conventional "Hopkins rod" endoscope (not shown) may be manipulated alongside the balloon dilation catheter 100 to aid in placement.

Figure 4:
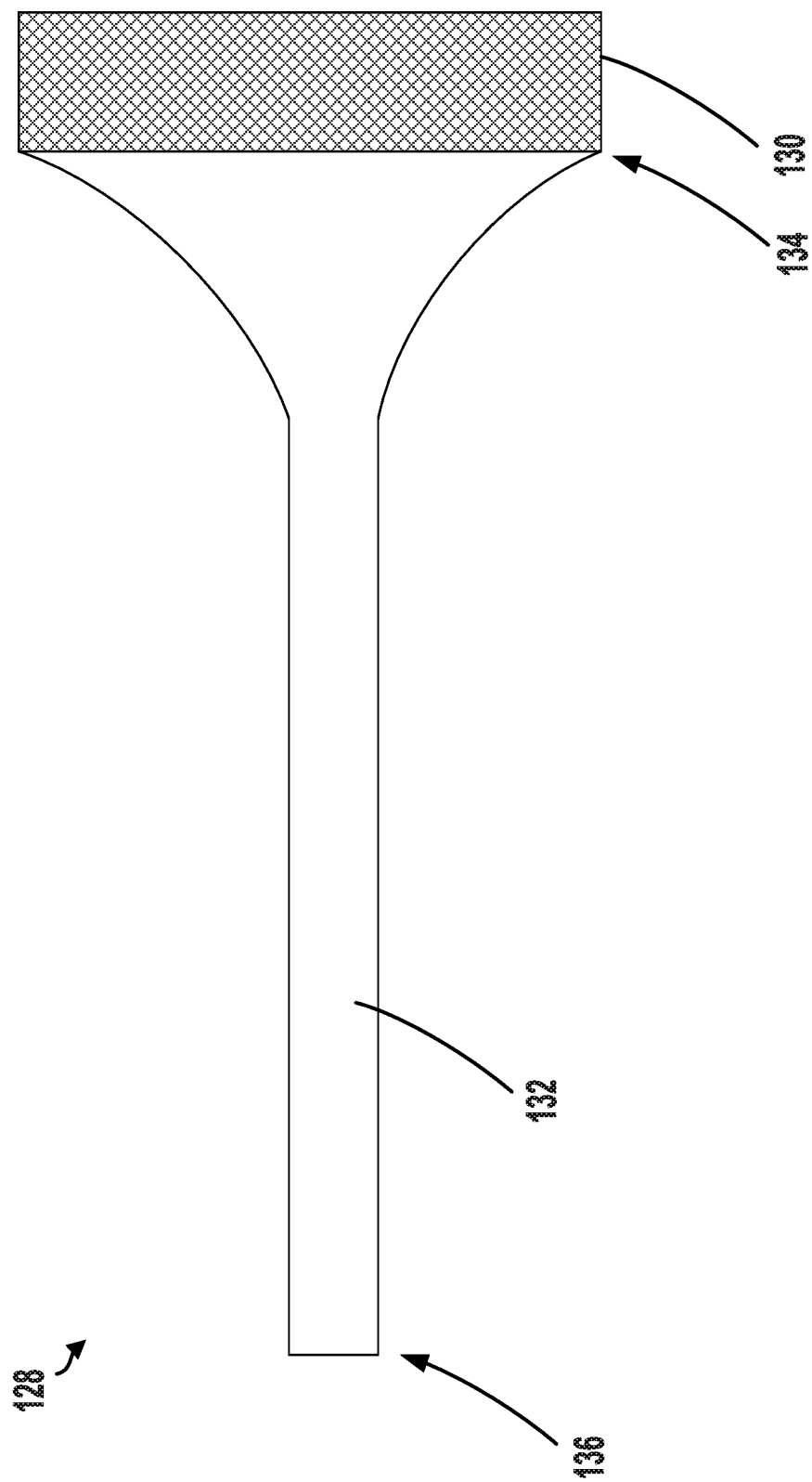
FIG. 4 is a light emitting guidewire, according to an example.
Figure 5A:
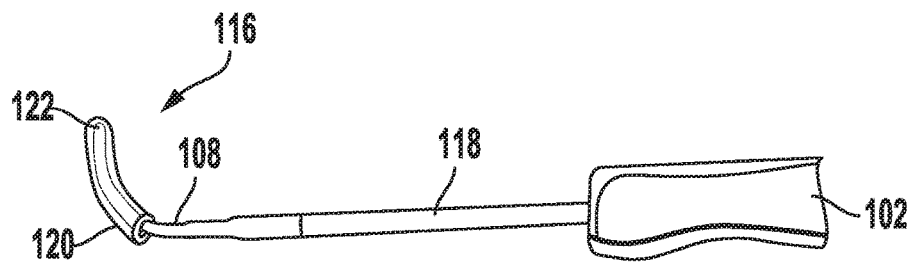
FIG. 5A is a side view of the distal end of the balloon dilation catheter of FIG. 1 with the distal end having a first example radius of curvature, according to an example.
Figure 5B:
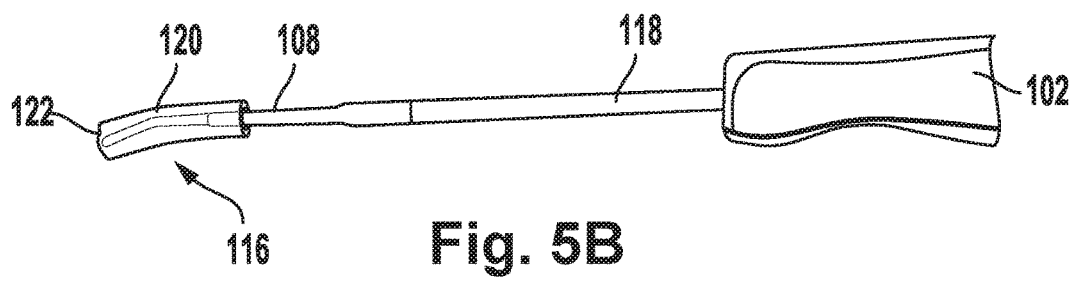
FIG. 5B is a side view of the distal end of the balloon dilation catheter of FIG. 1 with the distal end having a second example radius of curvature, according to an example.
Figure 5C:
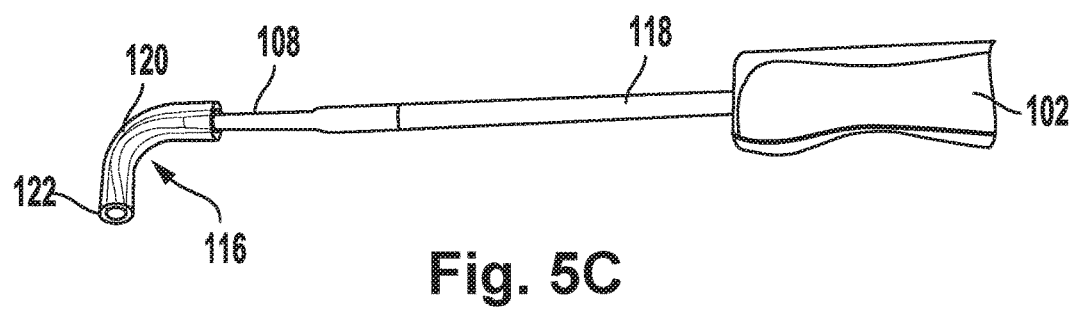
FIG. 5C is a side view of the distal end of the balloon dilation catheter of FIG. 1 with the distal end having a third example radius of curvature, according to an example.
Figure 5D:
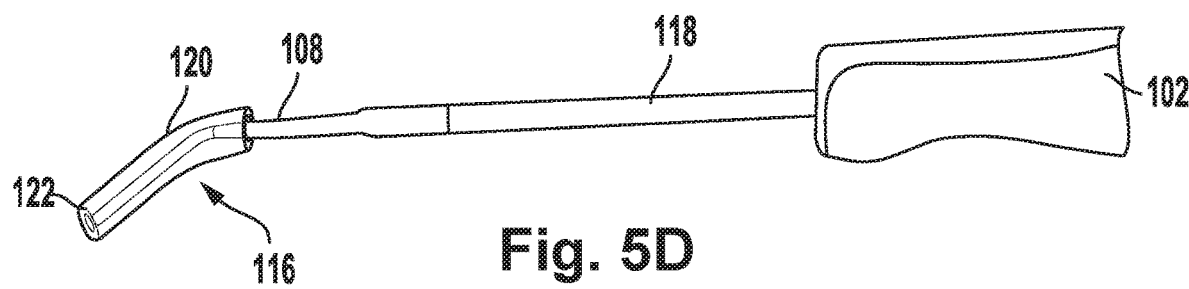
FIG. 5D is a side view of the distal end of the balloon dilation catheter of FIG. 1 with the distal end having a fourth example radius of curvature, according to an example.

In another example, as shown in FIG. 4, the guidewire may comprise a light emitting guidewire 128. Such a the light emitting guidewire 128 can include a light emitting diode 130 and an optical fiber 132 having a proximal end 134 and a distal end 136. A diameter of the proximal end 134 of the optical fiber 132 is less than a diameter of the distal end 136 of the optical fiber 132 such that the optical fiber 132 is flared at the distal end 136. During manufacture of the light emitting guidewire, the proximal end 134 of the optical fiber 132 may be pushed against a flat glass sheet to cause the optical fiber 132 to flare out to the desired shape. Such a flat glass sheet may be used due to its smooth surface, such that during flaring of the optical fiber 132 it leaves the proximal end 134 of the optical fiber 132 that is pushed against the flat glass sheet in a similar state to the polished distal end 136 of the optical fiber 132. Such arrangements provides a funnel or flare at the distal end 136 of the optical fiber 132 that mates with the light emitting diode 130 on an electronics board. This funnel or flare arrangement catches more of the light emitting diode 130 and channels it into the optical fiber 132, thereby increasing the efficiency of the light emitting guidewire 128. The more light that is caught, the less brightness needed from the light emitting diode 130 to reach a certain level, which results in longer battery life and less heat dissipated in the system.

In such examples, the light emitting guidewire 128 is used to help the operator identify portions of, or confirm a location within, a sinus cavity or sinus cavity drainage pathway. For example, in some embodiments, the distal end 136 of the light emitting guidewire 128 is inserted into a subject via a transnasal route and directed into a space or body lumen that a practitioner suspects is a part of the frontal drainage pathway that leads to a frontal sinus cavity. The operator directs the light emitting guidewire 128 into the suspected pathway and gently advances the instrument further into the body lumen. If the lumen leads to a frontal sinus cavity, the light from the distal tip will travel through the bone and tissue walls of the cavity and provide a transdermal or transcutaneous illumination pattern visible to the operator. In this way, the operator can confirm that the suspected body lumen is a part of the frontal drainage pathway and does in fact lead to a frontal sinus cavity. Manipulation of the light emitting guidewire 128 (e.g., rotation) will move the illumination pattern, further confirming the positioning the instrument in the frontal recess. Once confirmed as part of the drainage pathway, the operator can use the other embodiments of this invention discussed above to dilate all or parts of the pathway. Typically, the light emitting guidewire 128 would be removed from the target anatomy prior to the placement of any embodiment of the invention used to dilate all or parts of the pathway.

In another example, in some embodiments of the invention, light emitting guidewire 128 is used to confirm that a given location is within the maxillary sinus cavity. The operator directs the light emitting guidewire 128 to the location and looks for a visible transdermal or transcutaneous illumination pattern (e.g., an illumination pattern on the roof of the mouth or through the skin near the cheekbone). Once the pattern is observed, the operator then knows the given location is within the maxillary sinus cavity. If the pattern is not observed, the operator then knows the given location is unlikely to be within the maxillary sinus cavity. Other example procedures for different target anatomies are possible as well.

As shown in FIGS. 5A-5D, the radius of curvature of the curved portion 116 of the substantially rigid inner guide member 108 can range between about 6.35 mm and about 38.1 mm, and preferably between about 19.05 mm and about 31.75 mm. Each of the various curvatures illustrated in FIGS. 5A-5D may correspond to a unique treatment area in the sinus drainage pathways. For example, the various curvatures illustrated in FIGS. 5A-5D may correspond to the maxillary sinus, the frontal recess, the sphenoid, and the Eustachian tubes (not necessarily in that order). Accordingly, the balloon dilation catheter 100 may be a single use device that has a curved portion 116 that is specific to the desired treatment area in the sinus. In one example, the substantially rigid inner guide member 108 is removably coupled to the handle 102, such that the substantially rigid inner guide member 108 can be replaceable or modular elements that can be positioned inside the shaft 118 and inserted into the handle 102 in a press-fit type sealing arrangement. In another example, the entire balloon dilation catheter 100 is a single use system.

Figure 6:
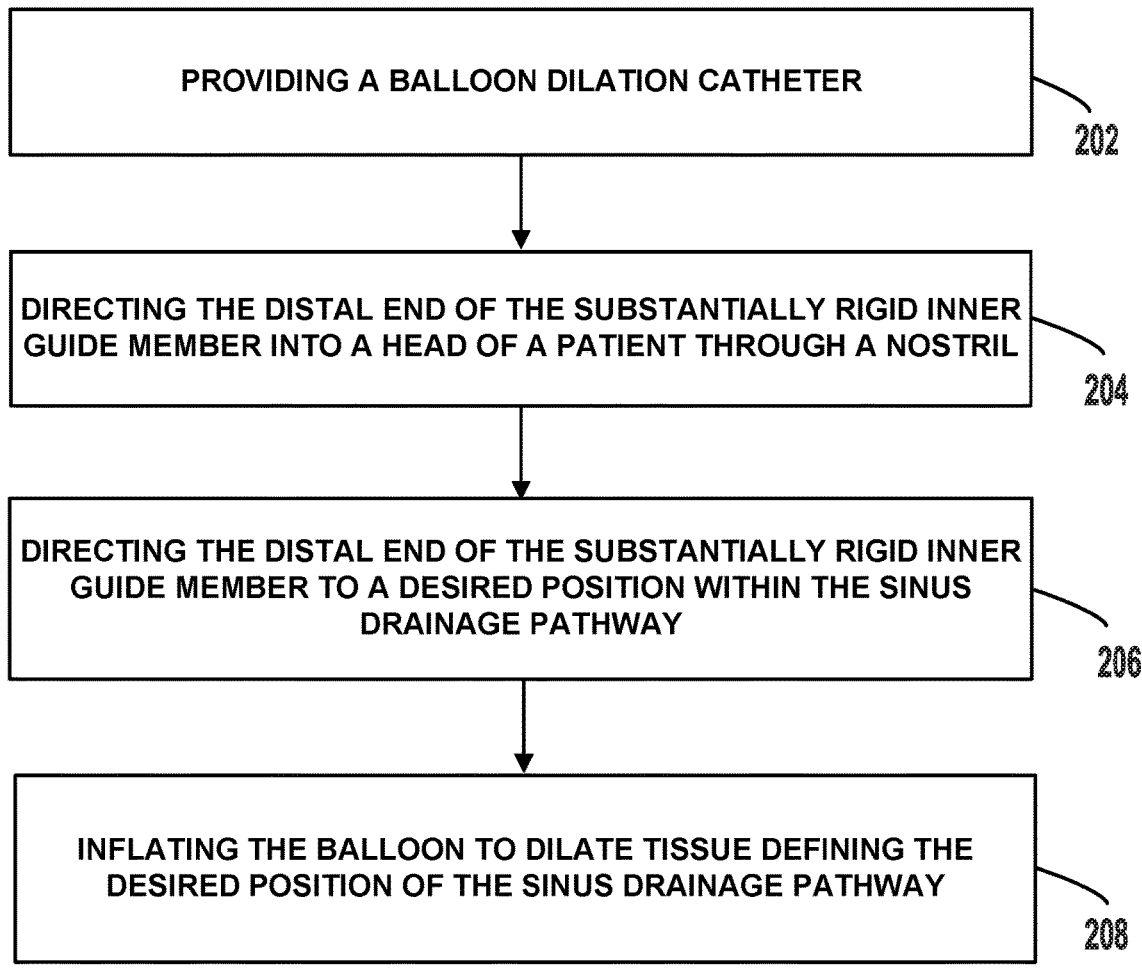
FIG. 6 depicts a flowchart for a method of treating a sinus drainage pathway of a patient, according to an example

Referring now to FIG. 6, a flowchart for a method 200 of treating a sinus drainage pathway of a patient is shown according to an example. The method steps of method 200 may be carried out at least in part by the balloon dilation catheter 100 as described above in relation to FIGS. 1-5D. Method 200 may include one or more operations, functions, or actions as illustrated by one or more of blocks 202-208. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 6, at block 202, the method 200 includes providing the balloon dilation catheter of any of the examples described above in relation to FIGS. 1-5D. At block 204, the method 200 includes directing the distal end of the substantially rigid inner guide member into a head of a patient through a nostril. At block 206, the method 200 includes directing the distal end of the substantially rigid inner guide member to a desired position within the sinus drainage pathway. At block 208, the method 200 includes inflating the balloon to dilate tissue defining the desired position of the sinus drainage pathway.

In one example of the method 200 described above, the method 200 further includes deflating the balloon, and removing the balloon from the nostril of the patient. In another example of the method 200, the desired position within the sinus drainage pathway comprises one of a maxillary sinus, a frontal recess, a sphenoid, and a Eustachian tube of the patient. Further, as described above, in one example the distal end of the substantially rigid inner guide member is intractable such that the radius of curvature of the curved portion of the substantially rigid inner guide member is constant and cannot be shaped by the operator.

In another example of the method 200 described above, the method 200 further includes positioning a guidewire within the lumen of the substantially rigid inner guide member. In one such example, the balloon dilation catheter further comprises a first port positioned at the proximal end of the handle, wherein the proximal end of the substantially rigid inner guide member forms a sealing arrangement with the first port, and wherein the first port comprises an adjustable connector configured to receive the guidewire. In such an example, the method 200 further includes adjusting a position of a distal end of the guidewire in relation to the distal end of the substantially rigid inner guide member via the adjustable connector. In another example, the guidewire is a tracking element for use with an image guided surgery system, the method 200 further includes determining, via the tracking element, a location of the distal end of the substantially rigid inner guide member, and adjusting a position of the distal end of the substantially rigid inner guide member based on the determined location. In yet another example, the guidewire is a light emitting guidewire, the method 200 further includes determining, via the light emitting diode, a location of the distal end of the substantially rigid inner guide member, and adjusting a position of the distal end of the substantially rigid inner guide member based on the determined location.

Figure 7:
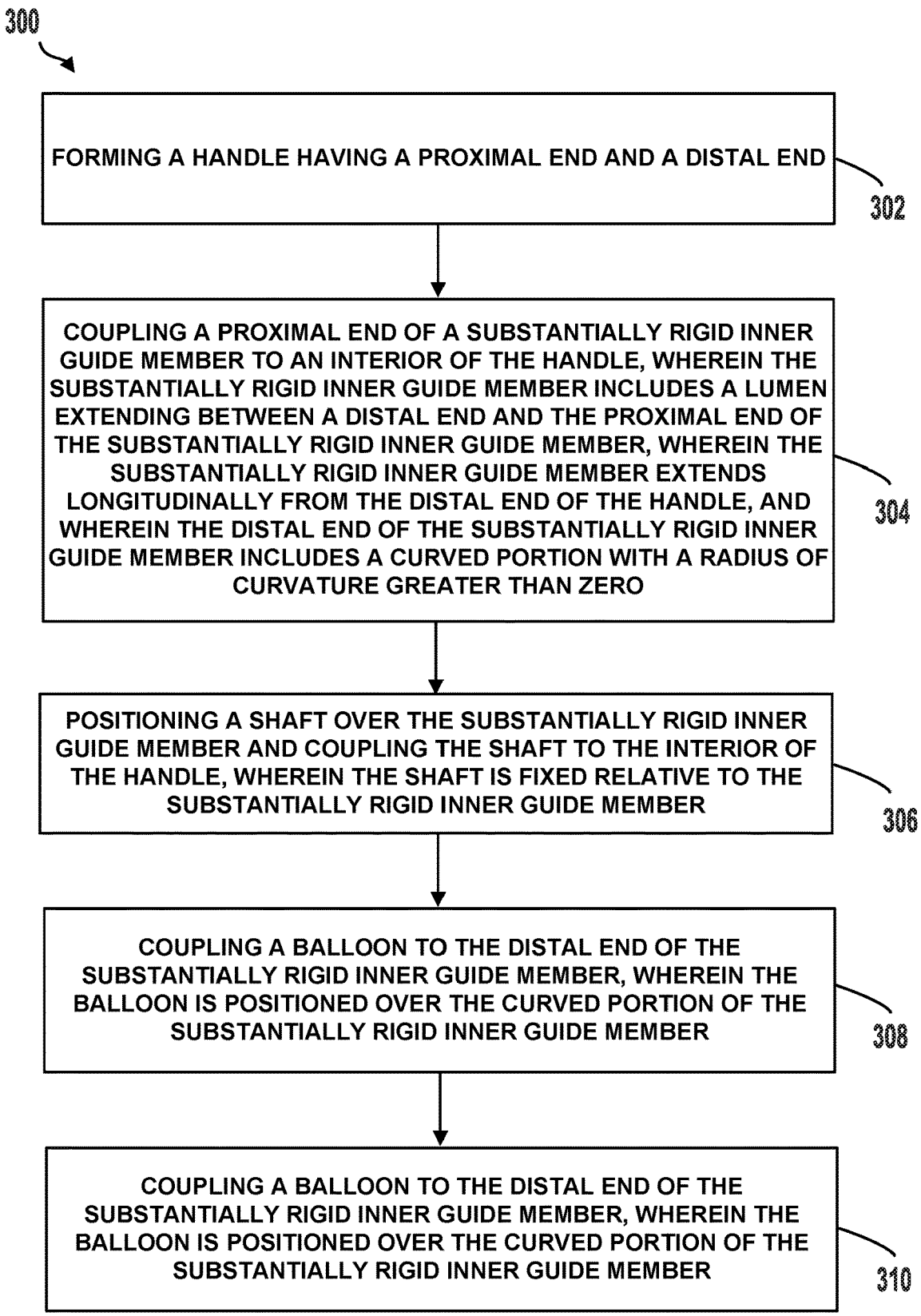
FIG. 7 depicts a flowchart for a method of manufacturing a balloon dilation catheter, according to an example.

Referring to FIG. 7, a flowchart for a method 300 for a method of manufacturing the balloon dilation catheter 100 of any of the examples described above is provided. The method steps of method 300 may be carried out to manufacture the balloon dilation catheter 100 as described above in relation to FIGS. 1-5D. Method 300 may include one or more operations, functions, or actions as illustrated by one or more of blocks 302-310. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

As shown in FIG. 7, at block 302 the method 300 includes forming a handle having a proximal end and a distal end. At block 304, the method 300 includes coupling a proximal end of a substantially rigid inner guide member to an interior of the handle, wherein the substantially rigid inner guide member includes a lumen extending between a distal end and the proximal end of the substantially rigid inner guide member, wherein the substantially rigid inner guide member extends longitudinally from the distal end of the handle, and wherein the distal end of the substantially rigid inner guide member includes a curved portion with a radius of curvature greater than zero. At block 306, the method 300 includes positioning a shaft over the substantially rigid inner guide member and coupling the shaft to the interior of the handle, wherein the shaft is fixed relative to the substantially rigid inner guide member. At block 308, the method 300 includes coupling a balloon to the distal end of the substantially rigid inner guide member, wherein the balloon is positioned over the curved portion of the substantially rigid inner guide member. At block 310, the method 300 includes forming a polymer ball tip at the distal end of the balloon from excess balloon material such that the polymer ball tip is directly coupled to the distal end of the balloon, wherein the polymer ball tip is further coupled to the distal end of the substantially rigid inner guide member.

In one example of the method 300 described above, the balloon is fixed relative to the shaft and further fixed relative to the substantially rigid inner guide member. In another example of method 300, the distal end of the substantially rigid inner guide member is intractable such that the radius of curvature of the curved portion of the substantially rigid inner guide member is constant and cannot be shaped by an operator. In another example of method 300, the substantially rigid inner guide member comprises a precipitation-hardened material, such as 17-7 precipitation-hardened stainless steel as a non-limiting example. In another example of method 300, the proximal end of the substantially rigid inner guide member is secured within the handle. In another example of method 300, the substantially rigid inner guide member is sealed to the handle. In another example of method 300, the substantially rigid inner guide member is sealed to the handle in a press-fit type sealing arrangement.

In another example of method 300, the method 300 further includes forming a first port positioned at the proximal end of the handle, wherein the proximal end of the substantially rigid inner guide member forms a sealing arrangement with the first port, and forming a second port positioned at the proximal end of the handle, wherein the second port is in fluid communication with the balloon via an inflation lumen. In one such example of method 300, the first port comprises an adjustable connector configured to receive a guidewire, wherein the adjustable connector enables an operator to adjust a position of a distal end of the guidewire in relation to the distal end of the substantially rigid inner guide member.

In another example of method 300, the method 300 further includes positioning a guidewire within the lumen of the substantially rigid inner guide member. In one such example of method 300, the guidewire is a tracking element for use with an image guided surgery system. In another such example of method 300, the guidewire is a light emitting guidewire, and wherein the method 300 further includes forming a light emitting diode, and forming an optical fiber having a proximal end and a distal end, wherein a diameter of the distal end of the optical fiber is less than a diameter of the proximal end of the optical fiber such that the optical fiber is flared at the proximal end.

In one example of the method 300 described above, when the balloon is coupled to the distal end of the substantially rigid inner guide member, there is an excess amount of polymer material that extends from the distal end of the substantially rigid inner guide member. In such an example, the polymer ball tip is then formed from that excess material, for example via a radio frequency (RF) weld. Other processes for forming the polymer ball tip are possible as well.

The methods described herein can be utilized effectively with any of the examples or variations of the devices and systems described above, as well as with other examples and variations not described explicitly in this document. The features of any of the devices or device components described in any of the examples herein can be used in any other suitable example of a device or device component.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and examples have been disclosed herein, other aspects and examples will be apparent to those skilled in the art. The various aspects and examples disclosed herein are for purposes of illustration and are not intended to be limiting, with the true scope being indicated by the following claims, along with the full scope of equivalents to which such claims are entitled. It is also to be understood that the terminology used herein is for the purpose of describing particular examples only, and is not intended to be limiting.

What is claimed is:

1. A balloon dilation catheter for dilating sinus drainage pathways comprising:
    a handle having a proximal end and a distal end, the handle configured to be gripped by an operator;
    a substantially rigid inner guide member having a distal end and a proximal end, wherein the substantially rigid inner guide member includes a lumen extending between the distal end and the proximal end of the substantially rigid inner guide member, wherein the substantially rigid inner guide member extends longitudinally from the distal end of the handle, and wherein the distal end of the substantially rigid inner guide member includes a curved portion with a radius of curvature greater than zero;
    a shaft arranged over the substantially rigid inner guide member;
    a balloon coupled to the shaft such that the balloon is fixed relative to the shaft, wherein the balloon is positioned over the curved portion of the substantially rigid inner guide member; and
    a polymer ball tip positioned at a distal end of the balloon, wherein the polymer ball tip is formed from excess balloon material such that the polymer ball tip is directly coupled to the distal end of the balloon, and wherein the polymer ball tip is distal of the distal end of the substantially rigid inner guide member.

2. The balloon dilation catheter of claim 1, wherein the balloon is fixed relative to the shaft and further fixed relative to the substantially rigid inner guide member.

3. The balloon dilation catheter of claim 1, wherein the distal end of the substantially rigid inner guide member is intractable such that the radius of curvature of the curved portion of the substantially rigid inner guide member is constant and cannot be shaped by the operator.

4. The balloon dilation catheter of claim 1, wherein the substantially rigid inner guide member comprises a precipitation-hardened material.

5. The balloon dilation catheter of claim 1, further comprising:
    a first port positioned at the proximal end of the handle, wherein the proximal end of the substantially rigid inner guide member forms a sealing arrangement with the first port; and
    a second port positioned at the proximal end of the handle, wherein the second port is in fluid communication with the balloon via an inflation lumen.

6. The balloon dilation catheter of claim 5, wherein the first port comprises an adjustable connector configured to receive a guidewire, wherein the adjustable connector enables the operator to adjust a position of a distal end of the guidewire in relation to the distal end of the substantially rigid inner guide member.

7. The balloon dilation catheter of claim 1, wherein a guidewire is arranged within the lumen of the substantially rigid inner guide member,
    wherein the guidewire is a light emitting guidewire, and
    wherein the light emitting guidewire comprises:
        a light emitting diode; and
        an optical fiber having a proximal end and a distal end, wherein a diameter of the distal end of the optical fiber is less than a diameter of the proximal end of the optical fiber such that the optical fiber is flared at the proximal end.

8. The balloon dilation catheter of claim 1, wherein the polymer ball tip and the lumen of the substantially rigid inner guide member comprise respective apertures that are configured for aspiration of blood or secretions.

9. A method of treating a sinus drainage pathway of a patient, comprising:
    providing a balloon dilation catheter of claim 1, wherein the balloon dilation catheter comprises:
        a handle having a proximal end and a distal end, the handle configured to be gripped by an operator,
        a substantially rigid inner guide member having a distal end and a proximal end, wherein the substantially rigid inner guide member includes a lumen extending between the distal end and the proximal end of the substantially rigid inner guide member, wherein the substantially rigid inner guide member extends longitudinally from the distal end of the handle, and wherein the distal end of the substantially rigid inner guide member includes a curved portion with a radius of curvature greater than zero,
        a shaft arranged over the substantially rigid inner guide member,
        a balloon coupled to the shaft such that the balloon is fixed relative to the shaft, wherein the balloon is positioned over the curved portion of the substantially rigid inner guide member, and
        a polymer ball tip positioned at a distal end of the balloon, wherein the polymer ball tip is formed from excess balloon material such that the polymer ball tip is directly coupled to the distal end of the balloon, and wherein the polymer ball tip is distal of the distal end of the substantially rigid inner guide member;
    directing the distal end of the substantially rigid inner guide member into a head of a patient through a nostril;

directing the distal end of the substantially rigid inner guide member to a position within the sinus drainage pathway; and inflating the balloon to dilate tissue defining the position of the sinus drainage pathway.

10. The method of claim 9, further comprising:

positioning a guidewire within the lumen of the substantially rigid inner guide member, wherein the balloon dilation catheter further comprises a first port positioned at the proximal end of the handle, wherein the proximal end of the substantially rigid inner guide member forms a sealing arrangement with the first port, and wherein the first port comprises an adjustable connector configured to receive the guidewire, the method further comprising:

adjusting a position of a distal end of the guidewire in relation to the distal end of the substantially rigid inner guide member via the adjustable connector.

11. The method of claim 9, further comprising aspirating blood or secretions through the lumen of the substantially rigid inner guide member, wherein the polymer ball tip and the lumen of the substantially rigid inner guide member comprise respective apertures that are configured for aspiration of the blood or secretions.

* * * * *